United States Patent [19]

Agrawal et al.

[11] Patent Number: 5,510,475
[45] Date of Patent: Apr. 23, 1996

[54] OLIGONUCLEOTIDE MULTIPLE REPORTER PRECURSORS

[75] Inventors: Sudhir Agrawal, Shrewsbury; Jin-Yan Tang, Worcester, both of Mass.

[73] Assignee: Hybridon, Inc., Worcester, Pa.

[21] Appl. No.: 320,835

[22] Filed: Oct. 7, 1994

Related U.S. Application Data

[63] Continuation of Ser. No. 610,541, Nov. 8, 1990, abandoned.

[51] Int. Cl.$^6$ .............................. C07H 21/00; C07H 21/04
[52] U.S. Cl. ................. 536/24.3; 536/24.31; 536/24.32
[58] Field of Search ............................... 536/25.3, 25.31, 536/25.32

[56] References Cited

FOREIGN PATENT DOCUMENTS

| 8703622 | 6/1987 | European Pat. Off. . |
|---|---|---|
| 0251283 | 1/1988 | European Pat. Off. . |
| 8802004 | 3/1988 | European Pat. Off. . |
| 8903849 | 5/1989 | European Pat. Off. . |
| 0373956 | 6/1990 | European Pat. Off. . |

OTHER PUBLICATIONS

Agrawal et al., *Tetrahedron Letts.* 31, 1543–1546 (1990).
McCurdy et al., *Nucleosides & Nucleotides* 10, 287–290 (1991).
Kuznetsova et al., Chemical Abstracts, vol. 109, Abstr. No. 170796a, p. 758, 1988, Bioorg. Khim., vol. 14, No. 4, pp. 490–499, 1988.
Godovikova et al., Chemical Abstracts, vol. 112, Abstr. No. 158803e, 1990, Bioorg. Khim., vol. 15, No. 9, pp. 1246–1252, 1989.
Amirkhanov et al., Chemical Abstracts, vol. 112, Abstr. No. 231403f, 1990, Bioorg. Khim., vol. 15, No. 12, pp. 1618–1626, 1989.
Seela et al. Nucl. Acids Res. 15(7):3113–3129, 1987.
Chemical Abstracts vol. 96, No. 11, Abstr. #79437m, Denny et al. J. Med. Chem. 25(3):276–315.
Chemical Abstracts vol. 109, No. 10, Abstr. #73982a, Gallot et al. Mol. Cryst. Liq. Cryst. 153(A):367–373, 1987.
Connolly, B. A. Nucleic Acids Rearch 15:3131–3139 (1987).
Coull et al. Tetrahedron Letters 27(34): 3991–3994 (1986).
Chu et al. Nucleic Acids Research 11:6513 (1983).
Agrawal et al., Nucleic Acids Res. 14: 6227–6245 (1986).
Agrawal, Tetrahedron Lett. 30: 7025–7028 (1989).
Cardullo et al., Proc. Natl. Acad. Sci. USA 85: 8790–8794 (1988).
Agrawal et al., J. Cell Biol. 107: 468 (1988).
Fidanza et al., J. Am. Chem. Soc. 111: 9117–9119 (1989).
Agrawal et al., Tetrahedron Lett. 31: 1543–1546 (1990).
Agrawal et al., Nucleic Acids Res. 18: 5419–5423 (1990).
Nelson et al., Nucleic Acids Res. 18: 7179–7186 (1989).
Misiura et al., Nucleic Acids Res. 18: 4345–4354 (1990).
Haralambidis et al., Nucleic Acids Research 18: 501–505 (1990).

*Primary Examiner*—Gary L. Kunz
*Attorney, Agent, or Firm*—Banner & Allegretti, Ltd.

[57] ABSTRACT

Oligonucleotides containing multiple free amino groups attached directly to the phosphorus atoms of the phosphodiester linkages having the structure shown below.

$$5'\ HO(CH_2)_n O - \left[ \begin{array}{c} O \\ \| \\ P-O(CH_2)_a O \\ | \\ NH \\ | \\ (CH_2)_b \\ | \\ NH_2 \end{array} \right]_z \begin{array}{c} O \\ \| \\ P-O-D(_pD)_t \\ | \\ NH \\ | \\ (CH_2)_c \\ | \\ NH_2 \end{array}\ 3'$$

wherein
  D= a ribonucleoside or deoxyribonucleotide;
  p= a 5' to 3'-phosphodiester or phosphoramidate linkage;
  n= 1 to 20;
  a= 1 to 20;
  b= 1 to 20;
  c= 1= 20;
  z= 0 to 20;
  t= 1 to 100; and
wherein
  for each repeating unit, "a" represents the same number or a different number than that number represented by "a" in every other repeating unit; and for each repeating unit "b" represents the same number or a different number than represented by "b" in every other repeating unit.

Multiple reporter molecules can be incorporated into the oligonucleotide via the free amino groups allowing for increased probe sensitivity.

3 Claims, 2 Drawing Sheets

OLIGONUCLEOTIDE MULTIPLE REPORTER PRECURSORS

This invention was made with government support under cooperative grant number 401 124846 from the National Institutes of Allergies and Infectious Disease. The government has certain rights in the invention.

This application is a continuation of application Ser. No. 07/610,541, filed Nov. 8, 1990, now abandoned.

BACKGROUND OF THE INVENTION

1. Field of the Invention

The invention relates to modification of oligonucleotides for incorporation of single or multiple reporter groups. More particularly the invention relates to improved modified oligonucleotides which are functionally derivatized to increase sensitivity of detection. Such oligonucleotides are useful as probes for a variety of nucleic acid-based diagnostic and therapeutic applications based on their hybridization to specific complementary nucleic acid sequences.

2. Summary of the Related Art

The preparation and use of functionalized oligonucleotides for incorporation of reporter groups is known in the art.

Agrawal et al., Nucleic Acids Res. 14:6227–6245 (1986) discloses introduction of biotin and flourescent dyes at either the 5' or 3' end of oligonucleotide. See also Agrawal, Tetrahedron Lett. 30: 7025–7028 (1989).

Cardullo et al., Proc. Natl. Acad. Sci. USA 85:8790–8794 (1988); Agrawal et al., J. Cell Biol. 107:468 (1988); and Haralambidis et al., Nucleic Acids Res. 18:501–505 (1989) teach the introduction of fluorophores into oligonucleotides.

These methods suffer from the limited signal strength inherent in the presence of the single reporter molecule which is incorporated into each oligonucleotide.

Consequently, numerous investigators have attempted to develop methods which allow the introduction of multiple reporter groups into each oligonucleotide as a means of increasing sensitivity of procedures which use the oligonucleotide as probes.

Fidanza et al., J. Am. Chem. Soc. 111:9117–9119 (1989), teaches the incorporation of reporter groups at phosphorothioate linkages in the nascent oligonucleotide.

Agrawal et al., Tetrahedron Lett. 31:1543–1546 (1990), and Agrawal et al., Nucleic Acids Res. 18:5419–5423 (1990), disclose methods for labelling oligonucleotides based on incorporating primary amines at phosphodiester moieties as phosphoramidates.

Nelson et al., Nucleic Acids Res. 127:7179–7186 (1989), discloses multiple reporter group incorporation at 5' termini of oligonucleotide using phosphoramidite linkage to the oligonucleotide via N-Fmoc-$O^1$-DMT-$O^2$-cyanoethoxydiisopropylaminophosphinyl-3-amino- 1,2-propanediol, a fixed-length linker.

Misiura et al., Nucleic Acids Res. 18:4345–4354 (1990), discloses a method for incorporating multiple reporter groups on oligonucleotides via phosphoramidite linkage using a three carbon glyceryl attachment backbone to which the reporter group is connected by an ether-linked aminopropyl group, i,e., another fixed-length spacer.

Haralambidis et al., Nucleic Acids Research 18: 501–505 (1990), teaches linkage of multiple reporter groups solely to 3' ends of oligonucleotides using polyamide moieties connected to the 3' end of the oligonucleotides and lysine residues connecting the reporter groups to the polyamide moieties.

Although these methods are useful, they have many limitations. Spacing of reporter groups is a critical factor for increasing sensitivity of detection. The methods known in the art do not provide for controlled variation of the spacing of reporter groups and therefore may be limited in maximizing sensitivity. In addition, the chemistry in the known phosphoramidite methods is rather complex. While the use of polyamide and amino acid attachment means is amenable to some variation in spacing and involves a somewhat simpler chemistry, these attachment reagents due to inappropriate spacing can cause quenching of signal, at least with fluorescent reporter groups, thereby decreasing sensitivity.

There is, therefore, a need for improved methods for incorporating multiple reporter groups into oligonucleotide. Preferred improved methods would utilize a simpler chemistry than existing methods and would allow for controlled, variable spacing of reporter groups without causing quenching of signal.

BRIEF SUMMARY OF THE INVENTION

The invention relates to means for labelling oligonucleotides with single or multiple reporter molecules. More particularly, the invention provides methods and reagents for incorporating single or multiple reporter molecules into oligonucleotides in a manner that allows readily controlled variation of the spacing of the reporter groups, thereby increasing sensitivity of detection. Thus the invention also provides labelled oligonucleotides that are more readily detectable than labelled oligonucleotide produced by existing means. The invention achieves these important goals while utilizing a simpler chemistry than existing methods for incorporating reporter groups into oligonucleotides.

The method of the invention allows the attachment of multiple reporter groups to an oligonucleotide of defined sequence. The attachment is by way of H-phosphonate coupling, using two different types of linker molecules. Thus the invention provides reagents that are useful for producing multiply-labelled oligonucleotides.

One such reagent is the first linker which is derived from an alkanediol, and for purposes of the invention is known as a "phosphonate linker". Another is the second linker which is a diaminoalkane, and for purposes of the invention is known as a "diamino linker." Modified forms of these linkers, having one hydroxyl or amino functionality protected by a chemical group are useful reagents for the method of the invention. Such modified linkers, for purposes of the invention, are known as "protected phosphonate linkers" and "protected diamino linkers", respectively.

The invention provides means for attachment of multiple reporter groups to the 5' end, to the 3' end or to the normal or modified (basic) internucleoside linkages of the oligonucleotide, using the linker reagents described above. For labelling of 5' ends of oligonucleotides, support bound oligonucleotide is bound in consecutive cycles to multiples of the protected phosphonate linker by H-phosphonate linkage. The protected diamino linkers are then bound to the phosphonate linkers via phosphoramidate bonds to form a support bound oligonucleotide with a 5' repeating polymer having multiple protected amino functionalities. Upon release from the support using a standard deprotection step (see Gait, Oligonucleotide Synthesis, IRL Press, Oxford, 1984), an oligonucleotide is liberated that has at its 5' end a repeating polymer with multiple free amino functionalities. For purposes of the invention such a molecule is known as a "5' functionalized oligonucleotide". Multiple reporter groups are then added to the 5' functionalized oligonucleotides via the free amino functionalities. By similar principles, oligonucleotides with multiply-labelled 3' ends may be produced. In this case a phosphonate linker is first attached to a solid support, and a repeating polymer having multiple protected amino functionalities is built upon the linker as before. The oligonucleotide is then synthesized upon the free phosphonate terminus of the repeating polymer to produce a support bound oligonucleotide with a 3' repeating polymer having multiple protected amino functionalities. Upon release from the support, this produces an oligonueleotide that has at its 3' end a repeating polymer with multiple free amino functionalities. For purposes of the invention, such a molecule is known as a "3' functionalized oligonucleotide." Multiple reporter groups are then added to the 3' functionalized nucleotides via the free amino functionalities. Finally, the invention provides means for producing oligonucleotides that are coupled to multiple reporter groups at one or more internucleoside linkages. In this instance, the method is carried out as described for the synthesis of oligonucleotides with 5' multiple reporter groups, followed by fusion of the repeating polymer to the 3' end of another oligonucleotide. Alternatively, the method can be carried out as described for the synthesis of oligonucleotides with 3' multiple reporter groups, followed by release from the column and fusion of the repeating polymer to the 5' end of another oligonucleotide. Those skilled in the art will recognize that functionalized structures analogous to those described for 5' and 3' labelling of oligonucleotides can be produced by this method. For purposes of the invention, that functionalized structure attached to one or more repeating phosphodiester moiety polymers with free amino functionalities is known as an "phosphodiester moiety-linked functionalized oligonucleotide". Multiply labelled oligonucleotides are then produced by adding reporter groups to the free amino functionalities.

In each labelling method of the invention the spacing of the reporter groups may be precisely controlled by using phosphonate linkers or diamino linkers of particular lengths. Thus the invention provides means for producing oligonucleotides having multiple reporter groups at the 5' end, at the 3' end, or attached to an phosphodiester moiety, wherein the spacing of the reporter groups may be precisely varied. Other embodiments of the invention will be made apparent by the following detailed description, example and claims.

DETAILED DESCRIPTION OF THE SPECIFIC EMBODIMENTS

Figure 1:
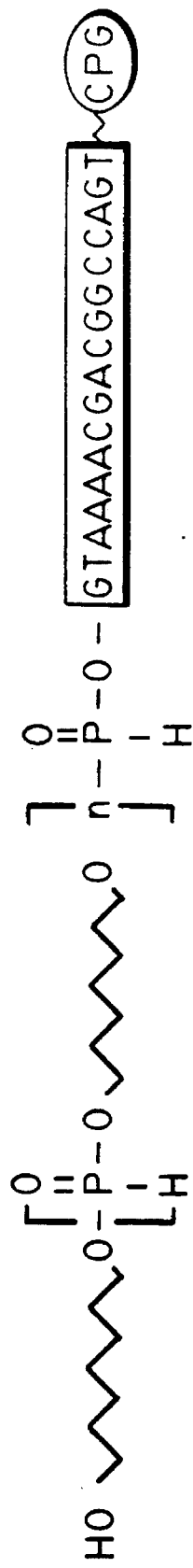
FIG. 1—After the assembly of the required sequence, couplings were carried out as described in Example 1, using a linker molecule and H-phosphonate chemistry. The oxidation was then carried out with $CF_3CONH(CH_2)_6NH_2$, followed by deprotection in ammonia.
Figure 1:
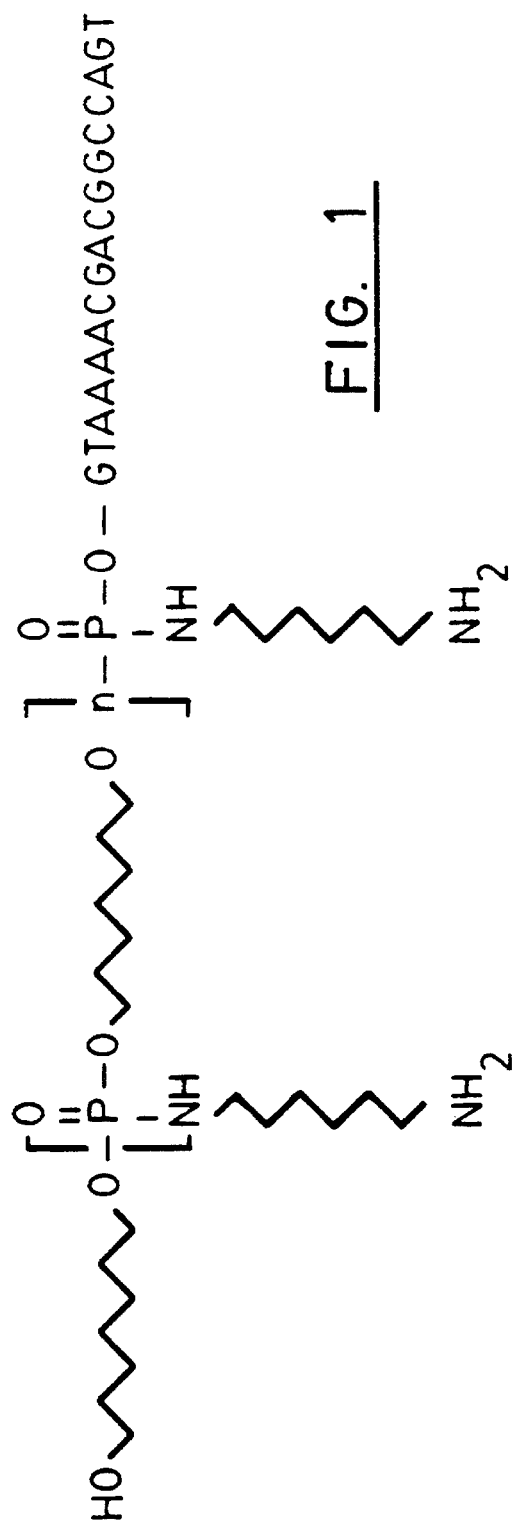

In a first aspect, the invention provides reagents that are useful for producing oligonucleotides having multiple reporter groups that are precisely spaced.

These reagents include protected linker molecules having at one end an H-phosphonate functionality and at the other end a protected hydroxyl group that is not reactive prior to the removal of the protective group. For purposes of the invention, such reagents are known as "protected phosphonate linkers". Protected phosphonate linkers according to the invention are characterized by the structure

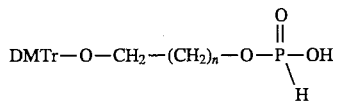

wherein

DMTr= an acid-labile protective group, such as dimethoxytrityl and n= 1 to 20.

Such protected phosphonate linkers according to the invention arc synthesized by treating an alkanediol with a salt of an acid-labile protective group, such as dimethoxytyl chloride to yield a protected derivative, followed by converting the protected derivative to the corresponding H-phosphonate by standard procedures.

Another reagent according to the invention is a protected linker molecule having at one end a free amino group, and at the other end a protected amino group that is not reactive prior to removal of the protective group. For purposes of the invention, such reagents are known as "protected diamino linkers". Protected diamino linkers according to the invention are characterized by the structure

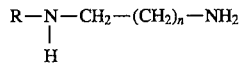

wherein

R=a base-labile group n= 1 to 20.

Such protected diamino linkers according to the invention are synthesized by protecting one amino group of a diaminoalkane with a base labile group under controlled conditions. (See Agrawal and Tang, Tetrahedron Lett. 31: 1543–1546 (1990)).

Another reagent provided by the invention is an oligonucleotide of defined nucleotide sequence having at its 5' end a repeating polymer having multiple free amino functionalities. For purposes of the invention, such reagent is known as a "5' functionalized oligonucleotide". 5' functionalized oligonucleotides according to the invention are characterized by the structure

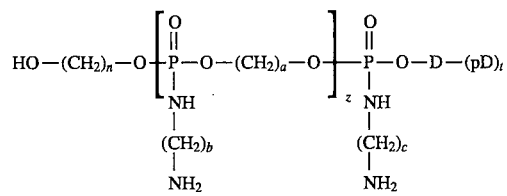

wherein

D=a ribonucleoside or deoxyribonucleoside, p= a phosphodiester linkage or chemically modified analog linkage, n= 1 to 20,
a= 1 to 20,
b= 1 to 20,
c= 1 to 20,
z= 0 to 20,
t= 1 to 100, and
wherein for each repeating unit [in brackets] "a" may represent the same number or a different number than that number represented by "a" in every other repeating unit, and for each repeating unit [in brackets] "b" may represent the same number or a different number than that number represented by "b" in every other repeating unit.

5' functionalized oligonucleotides, according to the invention, can be synthesized in the following manner. A protected phosphonate linker is prepared by treating an alkanediol with a salt of an acid-labile protective group, such as dimethoxytrityl chloride to yield a protected derivative of the alkanediol, which is then converted to the corresponding H-phosphonate by standard procedures. (See Frochief and Matteucci, Nucleic Acids Res. 14:5399–5407 (1986)). An oligonucleotide of defined sequence is synthesized (e,g,, by standard phosphoramidite, phosphonate or phosphotriester chemistry) to yield a support-bound oligonucleotide. A protected phosphonate linker is then coupled with the free 5' hydroxyl group of the support-bound oligonucleotide using an H-phosphonate coupling cycle. (See Agrawal and Tang, Tetrahedron Lett. 31:1543–1546 (1990)). Additional phosphonate linkers are added through a series of deprotection and H-phosphonate cycles, with each cycle adding one phosphonate linker. The total number of cycles (and thus linkers) should equal the number of reporter groups to be added to the oligonucleotide. The support-bound oligonucleotide/phosphonate linker complex is then oxidized with a protected diamino linker to yield a support-bound oligonucleotide with multiple protected amino functionalities. (See Agrawal and Tang, supra.) The support-bound oligonucleotide with multiple protected amino functionalities is then converted into a free 5' functionalized oligonucleotide by deprotection with a deprotecting agent, such as aqueous ammonia.

Thus the invention provides a method for producing a 5' functionalized oligonucleotide, which method comprises generally the following steps:

(a) coupling with support bound oligonucleotide a protected phosphonate linker by an H-phosphonate coupling cycle, wherein the protected phosphonate linker is the product of a reaction between an alkanediol and a salt of an acid-labile protective group, such as dimethoxytrityl chloride, which product has further been converted to an H-phosphonate;

(b) repeating the coupling of step (a) at least once;

(c) oxidizing the support bound oligodeoxynucleotide with a protected diaminolinker to produce an oligonucleotide with protected amino functionalities; and (d) deprotecting the oligonucleotide to yield a 5' functionalized oligonucleotide.

Another reagent provided by the invention is an oligonucleotide that has at its 3' end multiple free amino functionalities. For purposes of the invention, such reagent is known as a 3' functionalized oligonucleotide. 3' functionalized oligonucleotides according to the invention are characterized by the structure

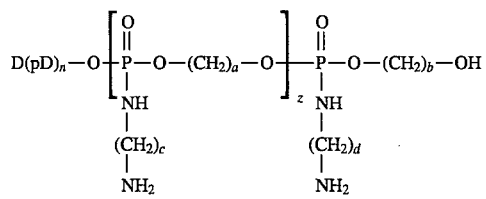

wherein

D=a ribonucleoside or deoxyribonucleoside, and p= a phosphodiester linkage or a chemically modified analog linkage, and n= 1 to 100, a=1 to 20, b=1 to 20, c= 1 to 20, d=1 to 20, z= 0 to 20, and wherein for each repeating unit [in brackets], "a" may represent the same number or a different number from that represented by "a" in every other repeating unit, and for each repeating unit [in brackets], "c" may represent the same number or a different number from that represented by "c" in every other repeating unit.

Such 3' functionalized oligonucleotides according to the invention are assembled in a manner that is analogous to that for the 5' oligonucleotides, except that a support-bound repeating structure having multiple protected amino functionalities is assembled using the same steps as before, but it is assembled first, beginning with linkage of a free phosphonate linker to the solid support by its free hydroxyl functionality. The oligonucleotide is then synthesized upon the repeating structure, beginning with an H-phosphonate coupling between the free phosphonate terminus of the repeating structure and the free 3' hydroxyl of the oligonucleotide. Completion of the oligonucleotide synthesis yields an oligonucleotide coupled to a repeating structure having multiple protected amino functionalities, the repeating structure in turn being bound to the support. This oligonucleotide/repeating structure complex is then converted into a 3' incorporation oligonucleotide by treatment with a deprotecting agent, such as aqueous ammonia.

Thus the invention provides a method for producing a 3' functionalized oligonucleotide, which method comprises generally the following steps:

(a) binding a free phosphonate linker to a support via the free hydroxyl of the phosphonate linker to yield a bound phosphonate linker;

(b) coupling to the bound phosphonate linker at least one more phosphonate linker, using an H-phosphonate coupling cycle to yield bound phosphonate linkers;

(c) oxidizing the bound phosphonate linkers with protected diamino linkers to produce a bound repeating structure having multiple protected amino functionalities;

(d) synthesizing an oligonucleotide that is attached to the bound repeating structure to produce a protected 3' functionalized oligonucleotide; and (e) deprotecting the amino functionalities to produce a 3' functionalized oligonucleotide.

The invention also provides useful precursors for the synthesis of 3' functionalized oligonucleotides and for 3' labelled oligonucleotides. Such precursors comprise the repeating structure of phosphonate linkers and diamino linkers described above, which are bound to a solid support suitable for oligonucleotide synthesis. The support-bound repeating structure may simply be an amino functionalized repeating structure or protected amino functionalized repeating structure, in which case an oligonucleotide may be synthesized attached to the structure, and may then be released (deprotected) to yield a free 3' functionalized oligonucleotide. Alternatively, the support-bound repeating structure may be a labelled repeating structure. In this case the amino functionalized support-bound repeating structure is synthesized, then the label is attached to the amino functionalities of the support-bound repeating structure. This embodiment requires the use as a label of a reporter group that is stable under oligonucleotide synthesis conditions, e.g., biotin, or a label that may be protected.

Another reagent provided by the invention is an oligonucleotide having multiple free amino functionalities coupled to it via one or more internucleoside phosphoramide linkages. For purposes of the invention, such reagent is known as a "phosphodiester moiety-linked functionalized oligonucleotide". Phosphodiester moiety-linked functionalized oligonucleotides according to the invention re characterized by the following structure

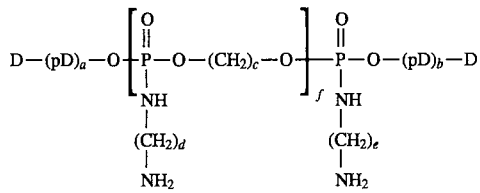

wherein

D= a ribonucleotide or deoxyribonucleoside, and p= a phosphodiester linkage or a chemically modified analog linkage, and a= 1 to 100, b= 1 to 100, c= 1 to 20, d= 1 to 20, e= 12 to 20, f= 0 to 20, and wherein for each repeating unit [in brackets], "c" may represent the same number or a different number from that represented by "c" in every other repeating unit, and for each repeating unit [in brackets], "d" may represent the same number or a different number from that represented by "d" in every other repeating unit, and for each repeating unit [in brackets],"e" may represent the same number or a different number from that represented by "e" in every other repeating unit.

Such phosphodiester moiety-linked functionalized oligonucleotides according to the invention may be synthesized by carrying out synthesis of a 5' functionalized oligonucleotide and then fusing another oligonucleotide to the 5' functionalized oligonucleotide via the free hydroxyl group on its terminal phosphonate linker. Alternatively a 3' functionalized oligonucleotide can be synthesized, then fused, via the free hydroxyl of its terminal phosphonate linker, to another oligonucleotide.

Thus the invention provides methods for producing an internucleoside phosphodiester moiety-linked functionalized oligonucleotide, comprising generally the following steps:

(a) coupling with support bound oligonucleotide a protected phosphonate linker by an H-phosphonate coupling cycle;

(b) repeating the coupling of step (a) according to the number of amino groups required;

(c) oxidizing the support bound oligodeoxynucleotide with a protected diaminolinker in the presence of carbon tetrachloride to produce an oligonucleotide with protected amino functionalities;

(d) continuing the oligonucleotide synthesis at a free end of the phosphonate linker; and (e) deprotecting the amino functionalities to produce an internucleotide phosphodiester moiety-linked functionalized oligonucleotide.

In another aspect, the invention provides methods for producing oligonucleotides having at their 5' or 3' ends, or attached to one or more phosphodiester moieties, multiple reporter groups which confer upon the oligonucleotide detectability in a specific assay. Reporter groups according to the invention therefore include any molecules which confer upon the oligonucleotide detectability in a specific assay without unduly interfering with biological functions of the oligonucleotide, such as hybridization with a complementary nucleotide sequence or binding of a specific protein. Commonly used reporter groups will include biotin, various flourophores, enzymes, and molecules which are detectable by antibody binding or other ligand-receptor interactions.

These methods of the invention are practiced exactly as described for the production of 5', 3', or phosphodiester moiety-linked functionalized oligonucleotides, followed by coupling of the reporter group to the functionalized oligonucleotide via linkage with the free amino functionalities of the functionalized oligonucleotide. Thus, in these methods of the invention the spacing of the reporter groups can be manipulated by using different sizes of phosphonate linkers and diamino linkers.

The invention contemplates numerous obvious modifications that would be apparent to those skilled in the art. For example, structural modification of the repeating units of the invention could be made without undue experimentation by substituting linear or branched alkene, alkyne, cycloalkane, cycloalkene, cycloalkyne, aromatic or heterocyclic spacers for the alkane spacers used in the phosphonate linkers or diamino linkers. Also, the diamino linker may be replaced by polyamines. The diamino linker may also be replaced by a linker having a protected amino group at one end and a free hydroxyl group at the other end, whereby the linker becomes attached via its hydroxyl functionality to the phosphonate moiety of the phosphonate linker, forming a phosphotriester linkage. Yet another obvious modification is to use a phosphorothioate linker in place of the phosphonate linker and, in place of the diamino linker, a linker having a protected amino group at one end and a free sulfhydryl group at the other end, whereby the linkers can be joined via a disulfide linkage. An additional obvious modification is to use an aminoalkyl iodide in place of the diamino linker to react with a phosphodiester linkage to form a phophotriester linkage. Still another obvious modification in the methods of the invention is to incorporate reporter groups which are stable under oligonucleotide synthesis conditions, e.g., biotin, during the synthesis process, rather than thereafter.

In addition to embodiments containing the above, specifically enumerated obvious modifications, all embodiments containing obvious modifications are considered to be equivalents of the invention.

The following example is provided to further illustrate the invention and is not limiting in nature.

EXAMPLE

Figure 2:
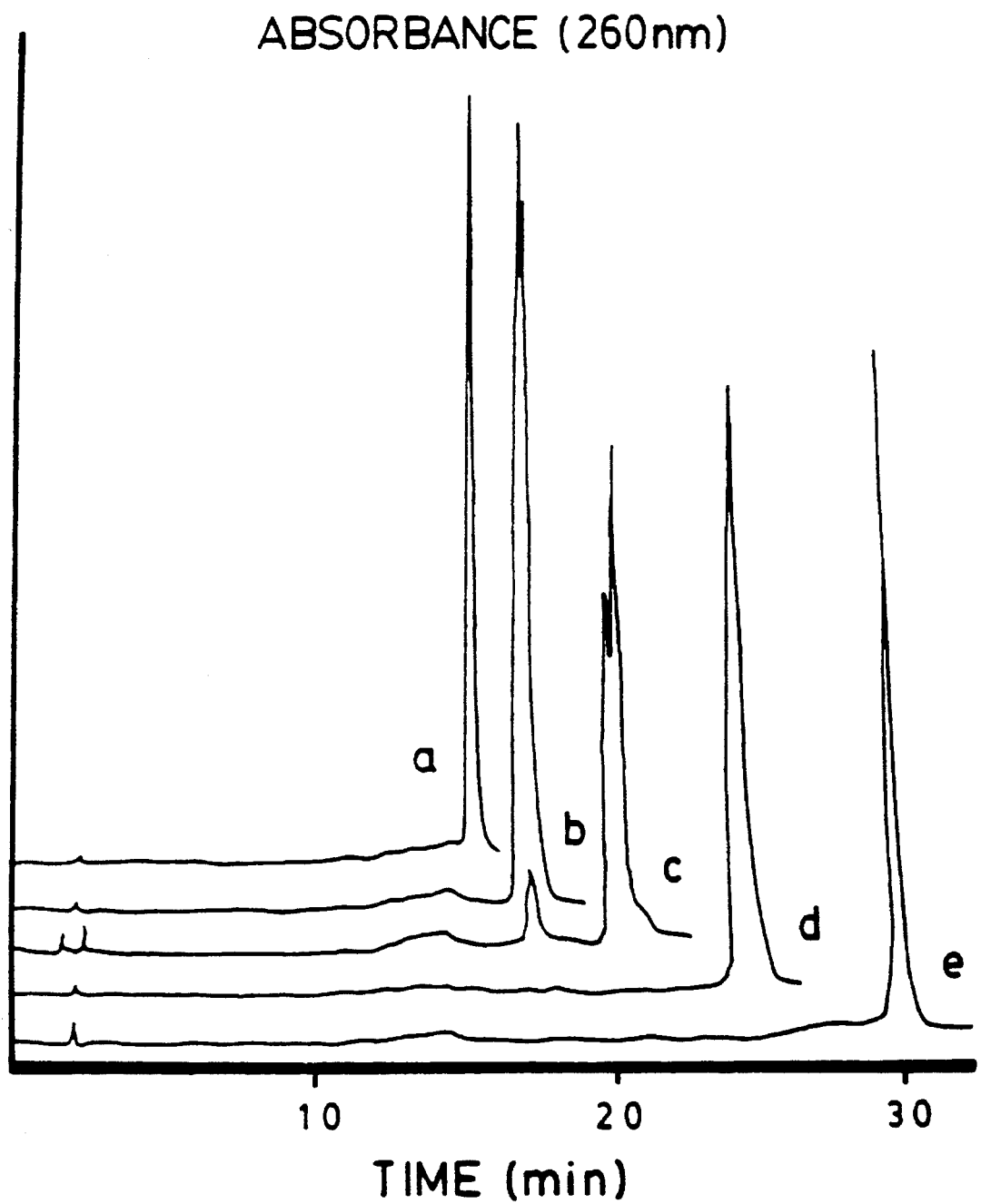
FIG. 2—Reversed phase HPLC analysis of (a) control 17-mer, (b) L(pN)-17-mer; (c) biotinylated L(pN)-17mer; (d) L(pN)L(pN)L(pN)-17mer; and (e) biotinylated L(pN)L(pN)L(pN)-17-mer. [L= hexanediol; (pN)= 6-aminohexylphosphoramidate]. HPLC was carried out using a Novapak $C_{18}$ column and buffers were 0.1M ammonium acetate containing (A) 0% acetonitrile and (B) 80% acetonitrile. The gradient was 0% for B for 2 minutes; 0–30% B in 23 minutes and 30–100% B in 10 minutes; flow rate 1.5 ml/minute.

Incorporation of Multiple Reporter Groups at the 5' end of an Oligodeoxynucleotide A six carbon non-nucleosidic linker was prepared by treating 1,6-hexanediol with 4,4'-dimethoxytrityl chloride (0.45 equiv.) in pyridine for two hours. The desired product, 6-(4,4'-dimethoxytrityl)-1,6-hexanediol was purified on a silica gel column in 90% yield, and was then converted to the corresponding H-phosphonate by a standard tris (1,2,4-triazole) phosphite procedure. To test the efficacy of the linker, a 17-mer sequence, GTAAACGACGGCCAGT, was assembled using normal phosphoramidite chemistry, followed by coupling with 6-(4,4'-dimethoxytrityl)-1,6-hexanediol-1, hydrogen phosphonate using a H-phosphonate coupling cycle. (See Agrawal and Tang, Tetrahedron Lett. 31:1543–1546 (1990)). The number of couplings depends on the number of amino-groups to be introduced. At the end of the assembly, support bound oligonucleotide was oxidized with N-1-trifluoroacetyl-diaminohexane. (See Agrawal and Tang, supra.) After deprotection with aqueous ammonia, the amino-functionalized oligonucleotide was reacted with biotin active ester using a published procedure. (See Agrawal et al., Nucleic Acids Res. 14: 6229–6245 (1986)). All oligonucleotides were checked by $C_{18}$ reverse phase HPLC (FIG. 2).

We claim:

1. A compound represented by the formula:

$$5' \ HO-(CH_2)_n-O-\left[\begin{array}{c} O \\ \| \\ P-O-(CH_2)_a-O \\ | \\ NH \\ | \\ (CH_2)_b \\ | \\ NH_2 \end{array}\right]_z \begin{array}{c} O \\ \| \\ P-O-D-(_pD)_t \\ | \\ NH \\ | \\ (CH_2)_c \\ | \\ NH_2 \end{array} \ 3'$$

wherein

D= a ribonucleoside or deoxyribonucleotide;

p= a 5' to 3'-phosphodiester or phosphoramidate linkage;

n= 1 to 20;

a= 1 to 20;

b= 1 to 20;

c= 1 to 20;

z= 0 to 20;

t= 1 to 100; and wherein for each repeating unit, "a" represents the same number or a different number than that number represented by "a" in every other repeating unit; and for each repeating unit "b" represents the same number or a different number than represented by "b" in every other repeating unit.

2. A compound represented by the formula:

$$5' \ D(pD)_n-O-\left[\begin{array}{c} O \\ \| \\ P-O-(CH_2)_a-O \\ | \\ NH \\ | \\ (CH_2)_c \\ | \\ NH_2 \end{array}\right]_z \begin{array}{c} O \\ \| \\ P-O-(CH_2)_b-OH \\ | \\ NH \\ | \\ (CH_2)_d \\ | \\ NH_2 \end{array} \ 3'$$

wherein

D= a ribonucleoside or deoxyribonucleotide;

p= a 5' to 3'-phosphodiester or phosphoramidate linkage;

n= 1 to 100;

a= 1 to 20;

b= 1 to 20;

c= 1 to 20;

d= 1 to 20;

z= 0 to 20; and wherein for each repeating unit, "a" represents the same number or a different number than that number represented by "a" in every other repeating unit; and for each repeating unit "c" represents the same number or a different number than represented by "c" in every other repeating unit.

3. A compound represented by the formula:

$$5' \ D-(pD)_a-O-\left[\begin{array}{c} O \\ \| \\ P-O-(CH_2)_c-O \\ | \\ NH \\ | \\ (CH_2)_d \\ | \\ NH_2 \end{array}\right]_f \begin{array}{c} O \\ \| \\ P-O-(pD)_b-D \\ | \\ NH \\ | \\ (CH_2)_e \\ | \\ NH_2 \end{array} \ 3'$$

wherein

D= a ribonucleoside or deoxyribonucleotide;

p= a 5' to 3'-phosphodiester or phosphoramidate linkage;

a= 1 to 100;

b= 1 to 100;

c= 1 to 20;

d= 1 to 20;

e= 1 to 20;

f= 0 to 20; and wherein for each repeating unit, "c" represents the same number or a different number than that number represented by "c" in every other repeating unit; and for each repeating unit, "d" represents the same number or a different number than represented by "d" in every other repeating unit.

* * * * *